US008663555B2

(12) United States Patent
Shiosawa

(10) Patent No.: US 8,663,555 B2
(45) Date of Patent: Mar. 4, 2014

(54) VACUUM STERILIZATION PROCESS AND DEVICES

(75) Inventor: Tadashi Shiosawa, Campinas/San Paulo (BR)

(73) Assignee: CISA S.p.A., Pomezia (Rome) (IT)

( * ) Notice: Subject to any disclaimer, the term of this patent is extended or adjusted under 35 U.S.C. 154(b) by 1086 days.

(21) Appl. No.: 12/537,546

(22) Filed: Aug. 7, 2009

(65) Prior Publication Data
US 2010/0028200 A1    Feb. 4, 2010

Related U.S. Application Data

(63) Continuation of application No. 10/556,621, filed as application No. PCT/EP2005/000357 on Jan. 14, 2005, now abandoned.

(30) Foreign Application Priority Data

Jan. 16, 2004    (BR) ..................................... 0400237

(51) Int. Cl.
*A61L 2/00*    (2006.01)
*A61L 2/18*    (2006.01)
*A61L 9/00*    (2006.01)
*A61L 2/20*    (2006.01)

(52) U.S. Cl.
USPC ................ 422/23; 422/22; 422/28; 422/33

(58) Field of Classification Search
USPC ........................ 422/297, 298, 23, 22, 28, 33
See application file for complete search history.

(56) References Cited

U.S. PATENT DOCUMENTS

| 4,764,351 | A | * | 8/1988 | Hennebert et al. | 422/292 |
|---|---|---|---|---|---|
| 5,667,753 | A | | 9/1997 | Jacobs et al. | |
| 5,961,921 | A | | 10/1999 | Addy et al. | |
| 6,159,422 | A | * | 12/2000 | Graves et al. | 422/22 |
| 6,261,518 | B1 | | 7/2001 | Caputo et al. | |
| 6,333,002 | B1 | | 12/2001 | Jacobs et al. | |
| 6,423,266 | B1 | | 7/2002 | Choperena et al. | |
| 6,488,889 | B1 | * | 12/2002 | Stahlecker et al. | 422/22 |
| 2003/0059340 | A1 | * | 3/2003 | Chien et al. | 422/30 |
| 2003/0086820 | A1 | * | 5/2003 | McDonnell et al. | 422/28 |
| 2003/0199846 | A1 | * | 10/2003 | Fowles et al. | 604/403 |

FOREIGN PATENT DOCUMENTS

| EP | 0 707 186 A1 | 4/1996 | |
|---|---|---|---|
| EP | 0707186 A1 | * 4/1996 | ............... F26B 5/00 |

OTHER PUBLICATIONS

PCT International Search Report for CISA S.R.L., Int'l Application No. PCT/EP2005/000357, Filed Jan. 14, 2005, Dated Apr. 20, 2005.
U.S. Office Action, Jul. 31, 2008, for Tadashi Shiosawa, U.S. Appl. No. 10/556,621, filed Jan. 23, 2006.
U.S. Office Action, Feb. 20, 2009, for Tadashi Shiosawa, U.S. Appl. No. 10/556,621, filed Jan. 23, 2006.

* cited by examiner

*Primary Examiner* — Regina M Yoo
(74) *Attorney, Agent, or Firm* — Reising Ethington P.C.

(57) ABSTRACT

Vacuum sterilization process with the application of vapour of a mixture of peracetic acid with hydrogen peroxide and residual gas plasma from atmospheric air, excited by pulsed electrical discharge; operational devices and methods used in the sterilization process, preferably a process of sterilization in vacuum, dry, and at low temperature (room temperature).

8 Claims, 7 Drawing Sheets

VACUUM STERILIZATION PROCESS AND DEVICES

This application is a continuation of U.S. Ser. No. 10/556,621, filed Nov. 9, 2005, corresponding to International Application No. PCT/EP05/000357, filed Jan. 14, 2005, which claims priority of Brazilian Application No. PI 0400237-7, filed Jan. 16, 2004, the entire disclosures of which are incorporated by reference herein in their entirety.

TECHNICAL FIELD

The present invention relates to a sterilization process, operational devices and respective methods applied for the sterilization of various different items of apparatus and products, using vacuum techniques, the application of sterilizing gas and plasma. More particularly, this invention makes use of gas from a solution of peracetic acid or hydrogen peroxide evaporated under vacuum, with the partial separation of water from the solution for sterilization, as well as the use of plasma from residual atmospheric air for the elimination of residues, with temperature monitoring and control.

BACKGROUND ART

Among chemical methods of sterilization, the use of hydrogen peroxide and peracetic acid is acquiring considerable prominence. This is due to their bactericidal, sporicidal, and fungicidal properties, which have been known for many years (BAULDRY, M. G. C., The bactericidal, fungicidal and sporicidal properties of hydrogen peroxide and peracetic acid, *Journal of Applied Bacteriology, Oxford, Vol.* 54, pp. 417-423, 1983). Peracetic acid is used in aqueous solutions, as a vapour or spray, and is efficient in the sterilization of plastic packaging (RAMMERT, M., Aseptic cold fill: Experiences and developments, Industrie delle Bevande, Dreux, Vol. 25, No. 142, pp. 123-128, April 1996) and the disinfecting of industrial equipment, and is of particular interest in the food industry since it leaves a residue consisting of acetic acid, oxygen, water, and hydrogen peroxide.

There are commercial systems for sterilization, such as:
a) The Contitherm System, which applies hydrogen peroxide in the form of vapour which adheres to the surface in the form of a fine film of condensate, being activated with sterile hot air, as well as promoting the elimination of its residue;
b) The Freshfill System, which uses the sanitizing agent in the form of a spray. Jets of sterile hot air activate the peroxide and eliminate the residue; c) The Serc System uses a mixture of chlorinated water, hydrogen peroxide, and peracetic acid. The material remains in contact with the sanitizing agent for about 90 seconds. This is followed by rinsing with sterile water; d) The ethylene oxide sterilization system (ETO), largely used for sterilizing heat-sensitive materials with a high degree of penetrability of the materials, which requires heating up to 58° C. and can also use Freon gas in the process.

Despite the high diversity of the sterilization systems which use peracetic acid and hydrogen peroxide and ethylene oxide, there are still a number of problems of operational and financial nature, as well as risks of contamination of the materials and the environment during the process. For example, application in diluted form requires large volumes of the sanitizing liquid, the materials cannot be packed, and sterile water is required for the rinsing, as well as a clean area for drying, thus incurring in the risk of re-contamination.

If applied in the form of vapour or spray, the system requires air which is filtered, hot, and sterile, in order to activate and eliminate the residues. These systems incur high energy consumption, as a function of the use of heater devices. The process with ethylene oxide requires long periods of sterilization, as well as aeration, since this substance is highly toxic.

Sterilization with plasma is one of the most recent techniques for the sterilization of surgical instruments and represents a great number of advantages over the procedures referred to heretofore.

The plasma state of the material is obtained by means of electrical discharge in a high-voltage field, DC, AC, or pulsed, in gases at low pressure. The action of this field on the gas or vapour molecules results in the provision of sufficient energy to the charged particles (electrons and ions), and these begin to produce pairs of electron-ions as a result of collision with the neutral gas molecules. As a consequence, the formation takes place of ions, accelerated electrons, neutral types, free radicals, and excited atoms and molecules, as well as the emission of ultraviolet radiation. If the application of the field is stopped, the activated types recombine, forming other types or returning to their basic state.

One commercial application of sterilization by plasma is described by the STERRAD® system. In this process, the materials are placed in a chamber in which a vacuum is then created. A solution of hydrogen peroxide is injected and vaporised inside the chamber containing the items which are to be sterilized. After allowing for a certain amount of time for diffusion, the pressure in the chamber containing this vapour is reduced and a plasma is initiated, with radio frequency energy being provided in order to exterminate micro-organisms and remove residues. The process is completed by disconnecting the RF energy and admitting filtered gas (HEPA) into the chamber.

The Patent PI 9708498-0 (U.S. Pat. No. 628,965), entitled "Method of Sterilization in Environments with Restricted Diffusion" makes use of hydrogen peroxide vapour as the former material and electrical discharges by radio frequency to generate plasma. In this process, the articles which require sterilization in a restricted diffusion environment are exposed to a source of peroxide, which may be static flooding, spraying, condensation of hydrogen peroxide vapour or peracetic acid vapour, before exposure to a vacuum or in a vacuum followed by plasma. The difficulty with penetration of the hydrogen peroxide in the environment with restricted diffusion is due to the presence of water vapour which, because it reaches the area concerned first, has a higher vapour pressure, which turns it into a barrier to penetration by the hydrogen peroxide vapour.

The Patent PI 9504382-9 A (U.S. Pat. No. 320,932), with the title: "Method of Sterilization under Vacuum, Method of Evacuation of a Condensed Material, and Method of Drying", describes a method of drying under vacuum with the liquefaction to plasma of residual gas and sterilization by the injection of sterilizing gas and a radio frequency source applied for the generation of plasma with the sterilizing gas. After a period allowed for diffusion in the sterilization process, the sterilizing gas, which is highly oxidant, is evacuated from the chamber by a vacuum pump in order to obtain lower pressure levels and to generate a plasma from this vapour, excited by an RF source.

The methods represented in the commercial systems and patents referred suffer from the following disadvantages:
1. The electrical discharge with radio frequency (RF) for the excitation of the plasma requires impedance couplers in order to obtain better utilization of the power supplied to the plasma. Depending on the geometric shape of the electrodes and the articles which are to be sterilized, this coupling may prove difficult, and consequently incur losses of energy and heating of the source, as well as the cost of the RF source being increased excessively with the increasing of its power, so making the sterilization processes substantially more expensive;

2. Damage to the vacuum system, incurred by the action of highly reactive gases during the process of evacuation after the exposure period and the diffusion of the sterilizing gas. This consequently requires a substantial number of handling procedures in the vacuum system, and a reduction in the service life of these items of equipment; and 3. Inefficiency of the process of sterilizing areas of restricted diffusion due to the injection of the aqueous solution of hydrogen peroxide or peracetic acid in the plasma sterilization system. Due to the physical properties of the water, this is diffused such that in the first instance it dilutes the concentration of the sterilizing vapours in the areas with restricted movement.

BRIEF DESCRIPTION OF THE INVENTION

An object of the present invention is to provide a sterilization process which, in association with the operational devices and respective methods, differs from the commercial processes and patents referred to heretofore, and presents numerous advantages, being:

1.) The initial plasma, formed with the residual gas from filtered atmospheric air by means of the present process, is applied in order to establish an adequate temperature and to enhance the active principle of the sterilizing gas which is to be injected;

2.) The excitation of the plasma used is effected by means of a pulsed DC power source instead of the radio frequency (RF) source referred to in the documents referred to heretofore. The pulsed DC signal is especially selected so as to avoid excessive heating at the plasma generating electrode, and has the advantage over RF of not requiring impedance couplers. Consequently, the excitation of the plasma is simpler and is less dependent on the type of charge (metal, glass ceramics, or plastic) and the design format of the electrode. Another advantage is the lower cost of manufacture.

3.) The combined action of submitting to vacuum the articles which are to be sterilized, and then following this with the application of the vapour from the solution of the stabilized mixture of peracetic acid, hydrogen peroxide, and acetic acid, or even hydrogen peroxide solution, is sufficient to promote sterilization at the levels required for normal techniques, while the quantity of water in the applied vapour, present in the solution of the mixture of evaporated peracetic acid or peroxide, is the minimum possible.

4.) The reduction of the water in the sterilizing gas which is injected increases efficiency and allows for the penetration of vapour into the environment with restricted diffusion. In this innovative process, the separation of water from the solution of the peracetic acid mixture, before the injection of the gas, is carried out with evaporation under vacuum and heating;

5.) Evacuation of the residual vapour of the sterilizing gas by means of a vacuum pump of the liquid loop type after the period of time for diffusion and sterilization of the articles. As a departure from the previous processes, in which the sterilizing gas is evacuated by a high-vacuum pump in order to reduce the pressure and form plasma with this gas, with the present invention filtered atmospheric air is injected into the residual sterilizing gas, then evacuated with a vacuum pump of the liquid loop type, with the mixture being diluted in water. The cycle is repeated two or more times. After this operation, a mechanical vacuum pump is used to reduce the pressure to lower levels and to apply the plasma. One advantage of this operation is that it avoids the greater part of the gas, which is highly corrosive, from passing through the vacuum system and damaging it; and 6.) The plasma applied in the process is induced by means of a gaseous atmosphere obtained from successive dilutions of the sterilizing gas with filtered atmospheric air, the aim of which is solely the elimination and removal of the residues of the sterilizing gas from the materials at the end of the sterilization process, contrary to the forming of plasma from the vapour of the residual sterilizing gas, the aim of which is the sterilization and removal of the residues from the previous systems. One advantage of plasma formed with gas from residual filtered atmospheric air over plasma from the vapour of the sterilizing gas from the process referred to heretofore lies in the preservation of the vacuum system by doing away with the passage of the concentrated sterilizing gas through this system.

Some of the preferred applications of the present process of sterilization in association with the sterilization device and the respective operational methods of the present invention can be described as follows:

Sterilization in the medical and hospital sector of heat-sensitive products used is materials for prostheses and for catheter and endoscopy procedures, as well as for metallic materials such as scissors, surgical scalpels, gloves, masks, latex tubes, and plates for cell cultures (PS, PET, PC, glass);

Sterilization in the odontology sector of dental prostheses and surgical instruments;

Sterilization in the pharmaceutical and cosmetic sectors: Clothing, glassware, plastic packaging, and components, such as, for example, medicinal fungi and moulds;

Vacuum sterilization processes and exposure to the vapour of peracetic acid or hydrogen peroxide with plasma in the sterilization of plastic packaging;

Sterilization in the food sector: Packaging and dried foods such as, for example, mushrooms, seeds, and leaves, among other items.

As known, some articles do not require sterilization to the level which the plasma provides, and in many cases these articles cannot be exposed to the plasma, such as is the case of foods, i.e. mushroom or grain, or other associated products.

By way of a theoretical illustration, biological materials such as grains, seeds, and other foodstuffs may have hygroscopic characteristics, and accordingly an exchange of water is created between them and the air, principally in the form of vapour. In this way, micro-climates are established on the surfaces of the products, the states of which are influenced principally by the moisture content of the products.

In these micro-climates, the quantity of water available is expressed by the aqueous activity factor ($a_a$), which varies from 0 to 1. This factor is defined as being the ratio between the current pressure value of the water vapour in the microclimate and the pressure of the vapour on the surface of a piece of pure water, which represents the vapour pressure under conditions of saturated air. In this way, the moisture content defines the vapour pressure values and the factor $a_a$ on the surface of the product.

Accordingly, in the space formed between the grains during the storage period, referred to as the intergranular space, an environment is established of which the state and conditions are influenced principally by the moisture content of the grain mass, which may favour the development of microorganisms or not, something which depends on the factor $a_a$.

Fungi, also referred to as moulds or mildews, are multicellular filament micro-organisms which, if they infest grains or other foods, may produce toxic substances, such as micro-toxins. In the case of grains, infestation may occur during cultivation or in the post-harvest period.

Bacteria develop in the products, which have an aqueous activity greater than 0.90, although for fungi the values vary from 0.65 to 0.90, due to which the grains may have a moisture content from 14 to 22%. Accordingly, a drying process is used in the preservation of grains. This reduces the moisture content of the products to levels at which the aqueous activity does not favour the proliferation of fungi.

In situation of hygroscopic balance, the relative humidity of the intergranular air corresponds to 100 times the value of aqueous activity. For this situation, the relative humidity of the air is referred to as relative humidity of equilibrium and the humidity of the grains as humidity of equilibrium.

Accordingly, many of the articles harvested are stored with micro-organisms, such as fungi and bacteria, and it is therefore necessary, as a minimum, to sanitize them before sending them for consumption or packing, in such a way as to respect the standards in force.

By means of the novel process provided, the present invention allows for this sanitization to be carried out with in-house equipment, without the need for the use of plasma, and without the need for the articles which are to be sterilized (or sanitized) to be subjected to a vacuum in the interior of the chamber, they being duly exposed, when wrapped in non-woven fabric packaging and for a predetermined period of time, to the vapour from the mixture obtained by evaporation with heating of the solution of peracetic acid, hydrogen peroxide, and acetic acid, allowing for the diffusion of this vapour in association with a renewed exposure to subsequent vacuum to eliminate the micro-organisms present in the articles and without the need for exposure to plasma.

BRIEF DESCRIPTION OF THE DRAWINGS

To supplement this Description in such a way as to obtain a better understanding of the characteristics of the present invention, and according to a preferred embodiment of it, a set of Drawings is appended to the Description in which, in an explanatory and non-limitative manner, the following representations are provided.

DETAILED DESCRIPTION OF THE INVENTION

Figure 1:
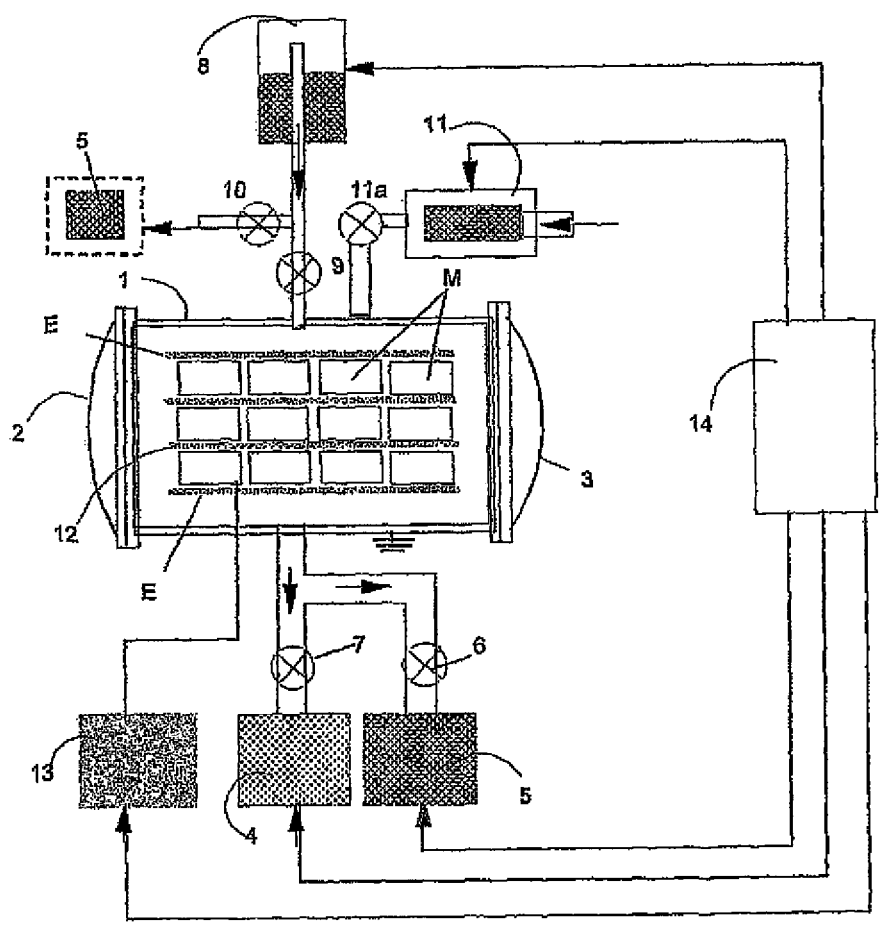
FIG. 1—Schematic diagram of the vacuum sterilization process with plasma.

With reference to the drawings, the present invention relates to a vacuum sterilization process with the application of steam of a mixture of peracetic acid with hydrogen peroxide and residual gas plasma from atmospheric air, excited by pulsed electrical discharge; to operational devices and methods used in the sterilization process, the process and devices being exemplified and illustrated in particular in a diagrammatical manner in FIG. 1, which comprises the sterilization of surgical and associated articles, and products in general (M), with the arrangement that, at the beginning of the sterilization process, the materials which are to be sterilized are arranged and subjected to a vacuum in a stainless steel chamber (1), with the option of one or two doors (2) and (3); connected to the chamber (1) is a vacuum system consisting of at least one mechanical vacuum pump (4) and at least one ring-type liquid vacuum pump (5), connected in parallel and linked to the said chamber by means of valves (6) and (7).

The process in question provides for a device (8) with an injector system for sterilizing gas, in which takes place the evaporation and separation of water from the solution of the mixture of peracetic acid or peroxide solution, and a system for the admission of atmospheric air, consisting of a HEPA® filter and dehumidifier (11), connected to the chamber (1) by valves (9) and (10) and to the dehumidifier (11) by a valve (11a). Internally, the chamber (1) is provided with a stand (12), consisting of level surfaces which, as well as serving as support for the articles (M) which are to be sterilized, also include the electrodes (E) at which the plasma for the sterilization is formed. Each of the electrodes (E) on the stand (12) is electrically connected to a power source which generates a pulsed DC signal (13), responsible for the supply of the energy for the excitation of the plasma.

The process is automatic, being controlled by a programmable logic controller (14), which manages the operational sequence of sterilization as well as monitoring and controlling the procedures and possible variables in relation to the materials used in the sterilization and in relation to the articles (M) which are to be sterilized, so optimising the operational time of the process.

Figure 4A:
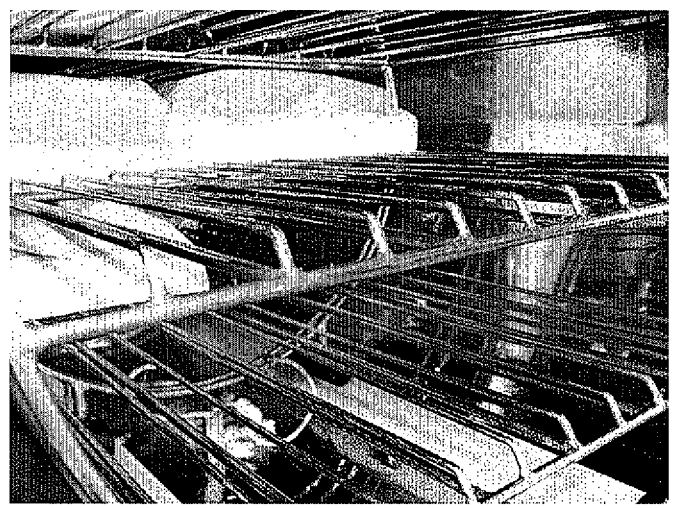
FIG. 4—Preferred embodiment of the configuration of the electrode stand developed for the homogenous distribution of plasma in the interior of the chamber in such a way as to keep the plasma close to the materials which are to be sterilized, where FIG. 4A refers to a photo of the electrode stand
FIG. 4B represents a schematic diagram of a side view of the electrode stand.
Figure 4B:
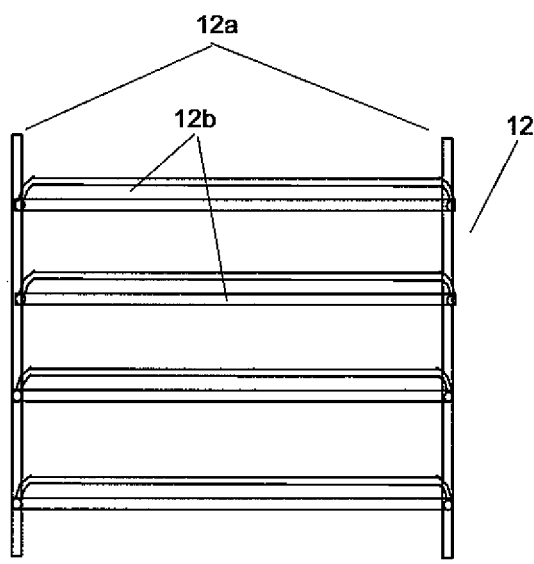

The configuration of each electrode which is located on the stand (12) (FIG. 4) has been developed in such a way as to cause a homogenous distribution of the plasma in the interior of the chamber, as well as in order to keep the plasma close to the articles (M) which are to be sterilized.

The preferred configuration of each electrode (E) on the stand (12) comprises two parallel shafts (12a) with segments (12b) in between, which can be configured as squares, spirals, or any other suitable shape to accommodate the electrode proper, and allowing that, with regard to the materials mounted on the stand (12), the plasma is generated in the area closely surround the electrode (E).

Figure 5:
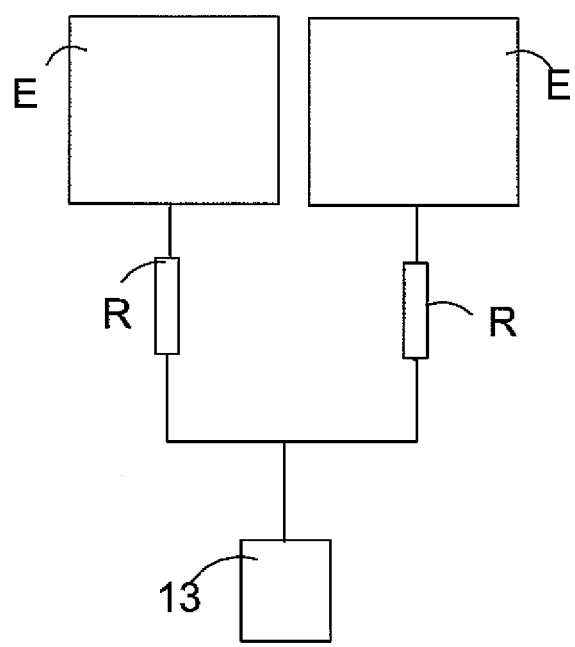
FIG. 5—Schematic diagram of the electrical connection between the electrode stand and the pulsed DC source.
Figure 6:
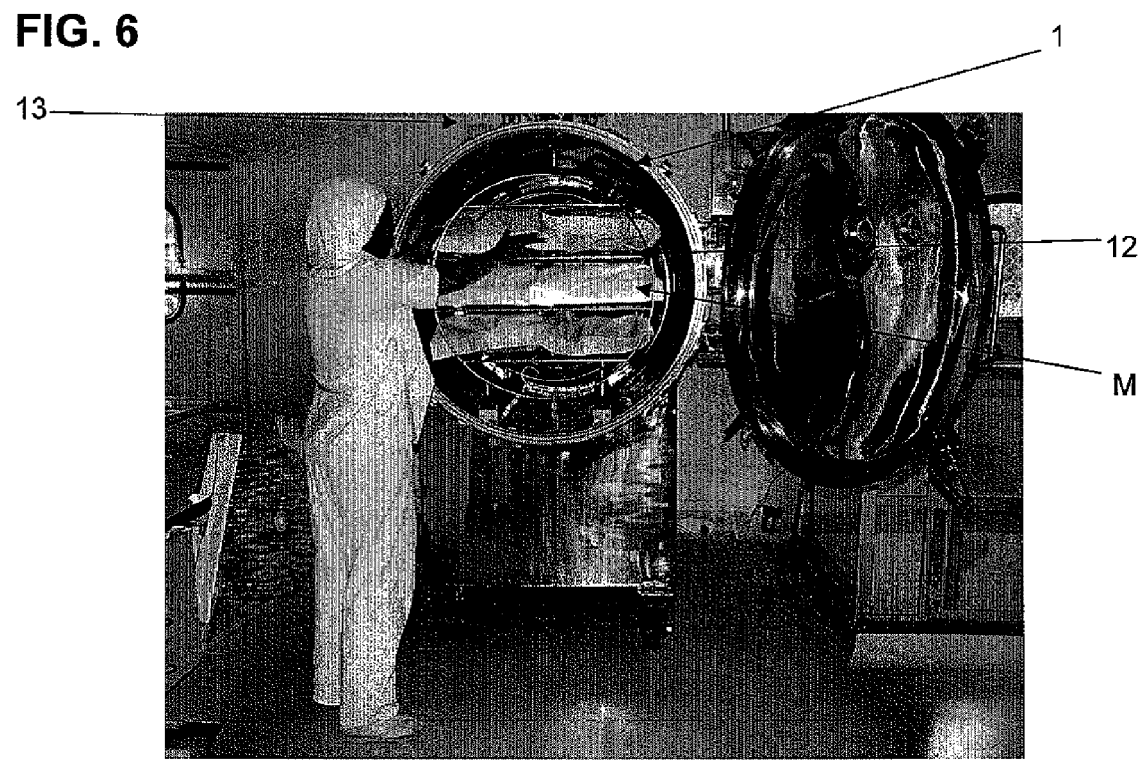
FIGS. 6 and 7 show photographs of the sterilization equipment in which are applied the innovative process, the devices, and the operational methods.
Figure 7:
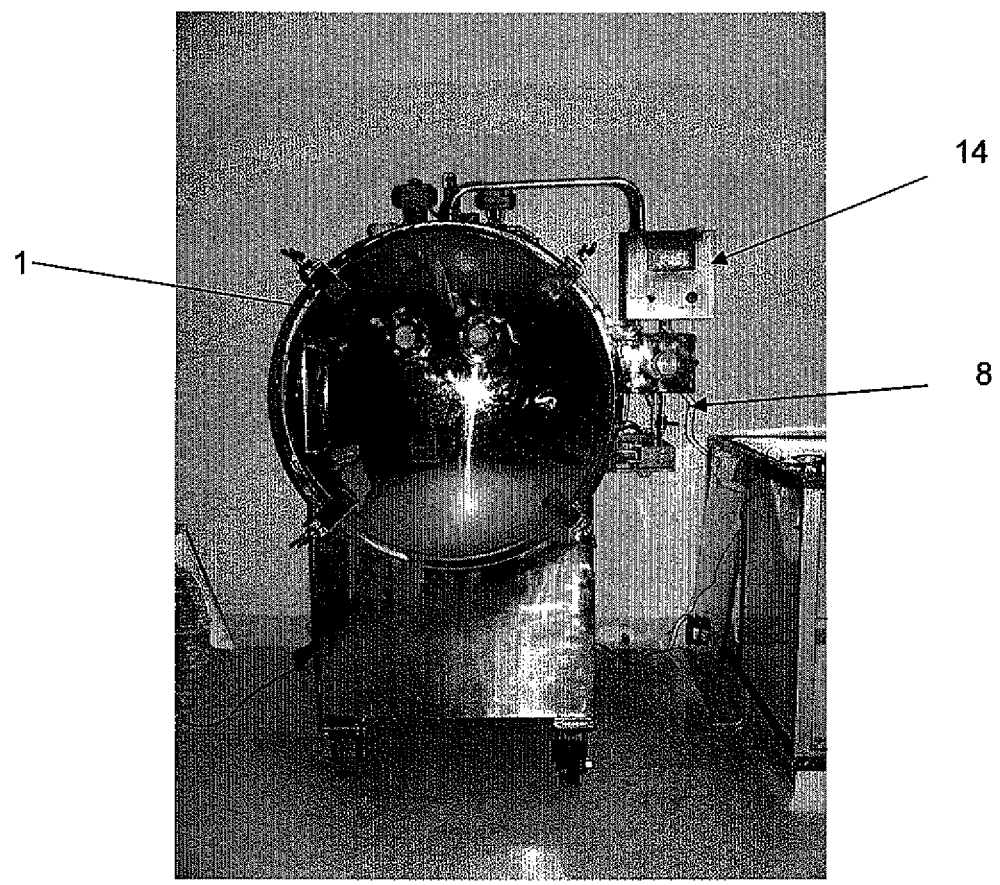

To put the method of plasma generation into effect, provision is made on the stands (12) for an electrical connection circuit between the electrodes (E) and the pulsed DC source (13) (see FIG. 5), this electrical connection between the DC source (13) and the electrodes (E) of the stand being connected in series with a resistor (R), the value of which may vary between 100 Ω and 5 KΩ. In this way it is possible to achieve the effects of concentration of electrical discharge and the collapse of the pulsed DC source.

Figure 2:
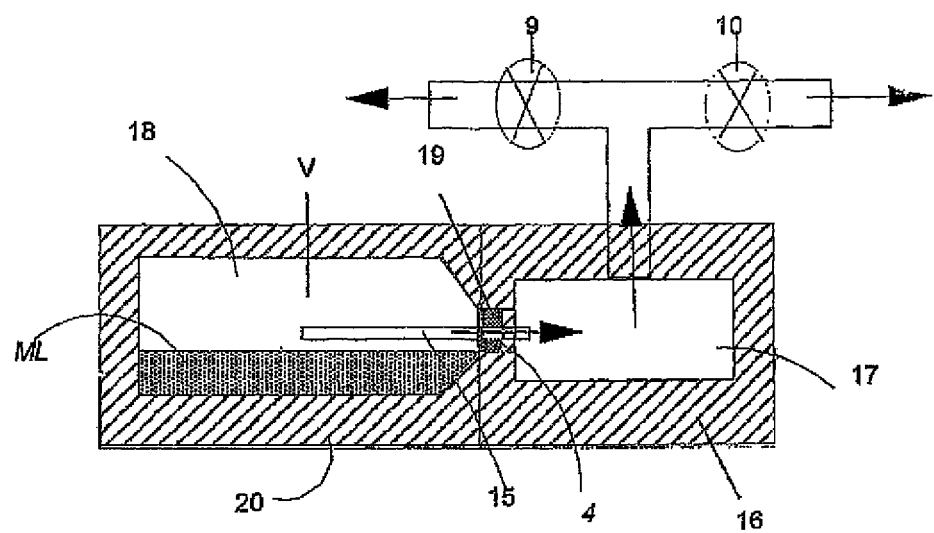
FIG. 2—Separator device fox separating water from the solution of the mixture of peracetic acid, hydrogen peroxide, and acetic acid, and an injector for the vapour of the remaining mixture.

The device (8) of FIG. 1, better illustrated in FIG. 2, is responsible for the application of the vapour from the solution of the liquid mixture of peracetic acid and hydrogen peroxide (ML) evaporated in a vacuum with heating and by the separation of the water from the solution, said device consisting for preference of a stainless steel needle (15) fixed in a base (16) which comprises in its interior an expansion chamber

(17) to which said needle is connected, said expansion chamber being provided with a means of communication with the valves (9) and (10).

Said device (8), more particularly in the area of the needle (15), is supplemented by ampoule (18) made of opaque material, of amber glass type or coated against luminosity, made of aluminium or other material, this ampoule (18) presenting one single passage which is blocked off by an inset blocking element (19) and which is connected to the base (16) by means of a guide piece (20).

When the ampoule (18) approaches close to the base (16), the needle (15) perforates the blocking element (19), allowing for a connection between the product present in the ampoule (18) and the expansion chamber (17), which in turn is connected to the sterilization chamber (1) via the valve (9), at the same as connecting to the liquid ring pump (5) via the valve (10).

The needle (15) is made of stainless steel; the ampoule (18) is made of amber glass or coated against luminosity or of aluminium or another equivalent material.

The operational method put into effect by the device (8) consists primarily of the water from the solution (ML) present in the ampoule (18) being evaporated in a vacuum with heating of the guide piece (20), this evaporation being conducted to the chamber (17) via the needle (15) and, consequently, to the liquid ring pump (5). Next, the remainder of the solution (ML) present in the ampoule (18) is also evaporated under vacuum with heating, and the sterilizing vapour is conducted to the chamber (1) via the valve (9), where it expands and diffuses onto the articles (M) which are to be sterilized.

The operational method of the process in question comprises the following steps:
a) First the articles (M), packed with non-woven surgical grade material, are placed on the stands (12);
b) The vacuum is induced in the chamber (1) by means of the liquid ring pump (5) and the valve (6), reducing the pressure to approximately 100 mbar;
c) Next, the pressure is reduced by the mechanical high-vacuum pump (4), and energy is supplied simultaneously in order for plasma to be generated, which continues to be applied until the obtaining of the sterilization conditions, and the pressure reaches approximately $2.10^{-3}$ mbar;
d) The water from the solution (ML) is separated and the sterilizing vapour is injected into the chamber (1);
e) Next, after the pumping to vacuum has been interrupted and the chamber isolated by the valve (7), the stabilized mixture of the solution (ML) of peracetic acid and hydrogen peroxide is vaporised in vacuum with heating;
f) A period of time is allowed to elapse in order for the vapour to diffuse in the articles (M) and to act on the micro-organisms;
g) After this waiting period, the process of the elimination of the remaining vapour and of the residues of the materials is started;
h) The filtered atmospheric air is admitted into the chamber via the HEPA® filter (11), raising the pressure to atmospheric pressure; and
i) Next, the pressure is again reduced by the liquid ring pump (5); items (h) and (i) are repeated one or more times;
j) The pressure is reduced by the mechanical vacuum pump to a pressure in the range from $5 \times 10^{-2}$ mbar to $5 \times 10^{-1}$ mbar;
k) Pulsed DC discharge plasma is generated from atmospheric air in order to complement the sterilization process and eliminate the residues; and
l) Filtered air is admitted by the HEPA® filter in order for the chamber (1) to be opened.

Due to the fact that some articles do not need to be, or cannot be, exposed to sterilization with plasma, such as foods of the mushroom type, grains, or other related products, the present invention, by means of this innovative process, allows for sterilization to be carried out at the level of sanitization in the equipment itself, without the need for the use of plasma, in which case the articles (M) which are to be sterilized (or sanitised) are arranged in stands (12), duly enclosed in packaging made of non-woven material. During a specified period of time, which may vary from article to article, these items are subjected to vacuum and to the vapour from the mixture obtained by evaporation with heating of the solution of peracetic acid, hydrogen peroxide, and acetic acid, allowing for the diffusion of this vapour in association with another exposure to the subsequent vacuum, so eliminating the micro-organisms present in the articles without the need for exposure to plasma.

The operational method for the sanitization/sterilization of articles without the need for plasma comprises the following steps:
a) The articles (M) are packed in non-woven material and arranged in the interior of the vacuum chamber (1);
b) They are subjected to vacuum;
c) The water from the solution (ML) is separated and the sterilizing vapour is injected into the chamber (1);
d) Next, after pumping to vacuum is interrupted and the chamber is isolated by the valve (7), the remaining mixture of the stabilized solution (ML) of peracetic acid and hydrogen peroxide is vaporised in vacuum with heating;
e) The exposure must be carried out during a certain period of time, depending on the material which is to be treated, allowing for the diffusion of the vapour over the article and so eliminating the micro-organisms;
f) The vapour is eliminated from the chamber by means of successive dilutions with atmospheric air and suction with the liquid ring pump;
g) The articles are again submitted to a vacuum from $1 \times 10^{-1}$ mbar to 100 mbar for the elimination of the residues; and
h) Filtered air is admitted through the HEPA® filter in order for the chamber (1) to be opened.

Despite the above detailed working examples, it is to be realized that the invention is not limited in its application to the details and steps described here. According to the knowledge of the skilled in the art, the invention can be worked in other embodiments. It should be understood that the terminology used here is intended for description and not for limitation purposes.

Plasma-Based Sterilization Process: Testing for Application in Medical Instruments Microbiological Test:

Initial Test

The evaluation of the process efficiency was done testing the microbial reduction of the *Bacillus Subtilis* var. *niger* (*globigii*), *Bacillus Stearothermophilus, E. coli* and *Pseudomonas Florence* Microorganisms.

*Bacillus Subtilis* (tested in an inox and plastic substrate)
*Bacillus Stearothermophilus* (tested in an inox and plastic substrate)
*E. coil* (tested in a plastic substrate)
*Pseudomonas Florence* (inox substrate)

Below are the test results using the spores of *Bacillus Subtilis* and *Bacillus Stearothermophilus*.

Sterilizer Load Conditions

For the sterilizer efficiency tests 2000 polypropylene jars wrapped in non-woven trilaminate cloth (60 g/m$^2$) were used as load.

Efficiency Test of Sterilization in Plastic Containers using Standard Kit Strips with *B. subtilis* and *B. stearothermophilus* for Validation The efficiency tests were performed with the same standard kit of spores of *B. subtilis* var *niger* (*globigii*) ATCC 9372, *B. stearothermophilus* ATCC 7953, approximate population of $1,0 \times 10^6$ UFC/strip, according to a certification issued by the Cefar laboratories, with the same kit used in the ETO sterilization process and thermal processes.

The testing was performed putting the strips with the microorganisms in the geometric center of the three stacks in each bag, arranged in three shelves two by two, as shown in the illustration. After the processing, the treated strips and the control samples with *B. subtilis* were put in a Triptone Soya Agar (TSA) medium and incubated under 35° C. for 48 hours to evaluate the surviving colonies, in any.

Results are presented below in Table 1:

TABLE 1

Testing with *B. Subtilis* var *niger* (*globigii*) ATCC 9372
Chamber loaded wit 2000 plastic pots

Figure 3:
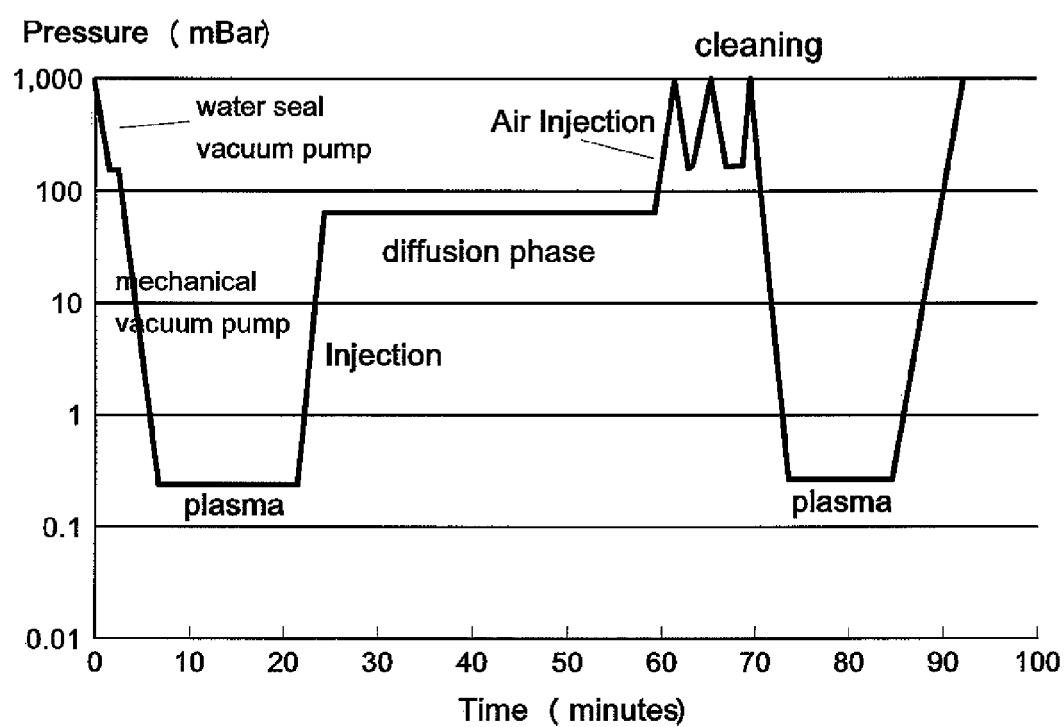
FIG. 3—Pressure graph as a function of the time of the sterilization operational cycle.

| Position of samples in chamber | Presence of microorganisms after processing |
| --- | --- |
| Front Upper End | Negative |
| Rear Upper End | Negative |
| Chamber Center (Front and Rear) | Negative |
| Front Lower End FIG. 3 | Negative |
| Rear Upper End | Negative |

Negative = absence of surviving colonies

TABLE 2

Testing with *B. Stearothermophilus* ATCC 7953
Chamber loaded wit 2000 plastic pots

| Position of samples in chamber | Presence of microorganisms after processing |
| --- | --- |
| Front Upper End | Negative |
| Rear Upper End | Negative |
| Chamber Center (Front and Rear) | Negative |
| Front Lower End FIG. 3 | Negative |
| Rear Upper End | Negative |

Conclusion: the plasma sterilization process was able to reduce an initial load of $10^6$ UFC spores of *B. subtilis* and *B. stearothermophilus* in every location inside the chamber.

Results 2

Efficiency results from microbiological tests performed on several items used in medicine and hospitals are shown. Amongst the diversity of items that can be sterilized by the plasma processing method, we chose to test the following items:

Endoscopy Cleaning Adapter
Microcollection device for haematological test
Endoscope Pliers
Fiber Optics laser cable
Connector and Cable for Electric Scalpel
Laser pen
Optical Endoscopy kit
Plastic draining tubes
Metallic tubing
Silicone tubing
Anoscopy
Vaginal Specula kit
Disposable Gynaecological kits
Plastic pliers
Scissors Every item was double wrapped in envelopes of non-waven trilaminate fabric and arranged inside the sterilization chamber.

The efficiency test were performed with the same standard kit of spores of *B. subtilis* var *niger* (*globigii*) ATCC 9372, approximate population of $1,0 \times 10^6$ UPC/strip, according to a certification issued by the Cefar laboratories, with the same kit used in the ETO sterilization process and thermal processes.

The testing was performed putting the strips with the microorganisms in the same bag containing the articles to be sterilized, as shown in the figure below. After the processing the treated strips and the control samples with *B. subtilis* were put in a Triptone Soya Agar (TSA) medium and incubated under 35° C. for 48 hours to evaluate the surviving colonies, if any.

Items formed of plastic and metal and requiring sterilization on the outer surfaces only are easily processed. We show below these items arranged on the TMS sheet right next to the test strips.

TABLE 3

Testing with *B. subtilis* ATCC 9372
Chamber loaded with hospital articles

| Chirurgical instruments | Presence of microorganisms after processing |
| --- | --- |
| M1 | Negative |
| M2 | Negative |
| M3 | Negative |
| M4 | Negative |
| M5 | Negative |
| M6 | Negative |
| M7 | Negative |

Conclusion: the plasma sterilization process was able to reduce an initial load of $10^6$ UFC spores of *B. subtilis* on all articles tested.

Polymeric and Metal tubing with internal diameter greater than 5 mm were tested by arranging the test strips loaded with $10^6$ UFC of *B. subtilis* spores in the mid-point of the tubing, as shown in the figures below.

TABLE 4

Testing with *B. stearothermophilus* ATCC 7953
Chamber loaded with hospital articles

| Chirurgical instruments | Presence of microorganisms after processing |
| --- | --- |
| M8 | Negative |
| M9 | Negative |
| M10 | Negative |
| M11 | Negative |
| M12 | Negative |
| M13 | Negative |
| M14 | Negative |

Conclusions

The plasma sterilization process here developed is able to promote sterilization at the required levels in almost all the thermo-sensitive material-based (latex, plastics, silicone, lenses) hospital items.

Inox steel items are easily sterilized.

The hardest items for sterilization are tubing, and the longer and narrower the tubing the harder is to get a proper sterilization level.

The sterilization process is able to process at the desired levels at open ended tubing with up to 5 mm in diameter and 3 m in length.

The invention claimed is:

1. A vacuum sterilization process for sterilization of articles, such that the sterilization process makes provision for the articles to be sterilized to be arranged and subjected to vacuum in a stainless steel chamber; wherein the process uses, connected to the stainless steel chamber, a vacuum system comprising at least one mechanical vacuum pump; wherein the process makes provision for a device comprising an injector system for sterilizing gas and a system for admission of atmospheric air, comprising a filter; wherein said process is an automated process controlled by a programmable logic controller and wherein said process is further characterized:

a) in application of vapour of a solution of hydrogen peroxide and residual gas plasma from atmospheric air, excited by pulsed electrical discharge;
   b) in that the vacuum system further comprises at least one liquid ring pump connected in parallel with said at least one mechanical vacuum pump and the vacumm system is linked to said stainless steel chamber by one or more valves;
   c) in that evaporation and separation of water from the hydrogen peroxide take place in the device;
   d) in that the system for the admission of atmospheric air further comprises a dehumidifier and wherein such system is connected to the stainless steel chamber by the one or more valves and to the dehumidifier by another valve;
   e) in that the interior of the stainless steel chamber is provided with a stand, composed of flat surfaces, which, as well as providing support to the articles which are to be sterilized, also comprise electrodes at which the residual gas plasma is formed for the sterilization process;
   f) in that the programmable logic controller is responsible for:
   reduction of pressure on the articles which are to be sterilized, by means of the liquid ring pump, which is employed prior to action of the mechanical vacuum pump, in order to attain a required pressure of the plasma;
   elimination of residual vapour from the solution of hydrogen peroxide by way of dilution with filtered atmospheric air and using the at least one liquid ring pump;
   application of the vapour from the solution of hydrogen peroxide evaporated in vacuum with heating and separation of the water from the solution;
   dilution of the vapour from the hydrogen peroxide by the injection of filtered air into the stainless steel chamber;
   provision of at least one stand, acting as a source electrode for generating a pulsed DC discharge, and the discharge of plasma close to the articles arranged on the at least one stand;
   generation of plasma from the residual atmospheric air with the excitation of pulsed DC in order to obtain an adequate temperature for sterilization;
   generation of pulsed DC discharge plasma from atmospheric air in order to complement the sterilization and elimination of residues; and
   the application of a vacuum within a pressure range of $5\times10^{-2}$ mbar to $1\times10^2$ mbar.

2. The vacuum sterilization process according to claim 1, wherein an operation method further comprises the following steps:

a) the articles, packed in non-woven surgical grade material, are placed on the at least one stand;
   b) the vacuum is induced in the chamber by means of the at least one liquid ring pump, reducing the pressure to approximately 100 mbar;
   c) the pressure is reduced by the mechanical vacuum pump, and energy is supplied simultaneously in order for plasma to be generated, which continues to be applied until the obtaining of sterilization conditions, and the pressure reaches approximately $2\times10^{-1}$ mbar;
   d) the water from the solution is separated and a sterilizing vapour is injected into the stainless steel chamber;
   e) after pumping to vacuum has been interrupted and the stainless steel chamber isolated by the valve, a stabilized solution of hydrogen peroxide is vaporised in vacuum with heating;
   f) a period of time is allowed to elapse in order for the vapour to diffuse in the articles and to act on microorganisms;
   g) the process of the elimination of the remaining vapour and of the residues of the materials is started;
   h) the filtered atmospheric air is admitted into the stainless steel chamber via a filter, raising the pressure to atmospheric pressure; and
   i) the pressure is again reduced by the at least one liquid ring pump; steps (h) and (i) are eventually repeated one or more times;
   j) the pressure is reduced by the mechanical vacuum pump to a pressure in the range from $5\times10^{-2}$ mbar to $5\times10^{-1}$ mbar;
   k) pulsed DC discharge plasma is generated from atmospheric air in order to complement the sterilization process and eliminate the residues; and
   l) the filtered air is admitted by the filter in order for the stainless steel chamber to be opened.

3. The vacuum sterilization process according to claim 2 wherein the solution of hydrogen further comprises peracetic acid.

4. The vacuum sterilization process according to claim 1 wherein the solution of hydrogen peroxide further comprises peracetic acid.

5. The vacuum sterilization process according to claim 1, wherein the pulsed DC voltage is applied to 10 KV and at a frequency of up to 250 KHz for the generation of plasma from atmospheric air at a pressure from $8\times10^{-2}$ to $1\times10^0$ mbar in order to begin and conclude the sterilization under vacuum and elimination of residues.

6. The vacuum sterilization process according to claim 1, wherein:

the water from the solution (ML) provided in an ampoule is evaporated in vacuum with heating of a guide element;
   the resultant evaporation is conducted to an expansion chamber via a needle;
   the evaporation present in the expansion chamber is conducted to the at least one liquid ring pump via at least one of said one or more valves connnecting the vacuum system for the admission of atmospheric air to the stainless steel chamber;
   the valve connecting the vacuum system for the admission of atmospheric air to the stainless steel chamber closes;
   the remnant of the solution present in the ampoule is evaporated under vacuum with heating;
   a sterilizing vapour is conducted to the expansion chamber via the needle;
   the sterilizing vapour present in the expansion chamber is conducted to the stainless steel chamber via at least one of said one or more valves connecting the vacuum system for the admission of atmospheric air to the stainless steel chamber, where it is expanded and diffused on the articles which are to be sterilized.

7. The vacuum sterilization process according to claim 1, wherein, for the plasma generation, the at least one stand comprise an electric connection circuit between the electrodes and a pulsed DC source, wherein said electrical connection circuit between the DC source and the electrodes of the stand is a connection in series with a resistor.

8. The vacuum sterilization process according to claim 7, wherein the resistor may vary between 100 Ω and 5 KΩ.

* * * * *